(12) United States Patent
Higuchi et al.

(10) Patent No.: US 7,470,525 B2
(45) Date of Patent: Dec. 30, 2008

(54) PROCESS FOR PRODUCING OPTICALLY ACTIVE 2-ALKYCYSTEINE, DERIVATIVE THEREOF, AND PROCESSES FOR PRODUCTION

(75) Inventors: Yasushi Higuchi, Tokyo (JP); Akinori Tanaka, Niigata (JP); Ryuji Hasemi, Niigata (JP); Masaki Sugita, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 323 days.

(21) Appl. No.: 10/579,772

(22) PCT Filed: Nov. 18, 2004

(86) PCT No.: PCT/JP2004/017140

§ 371 (c)(1),
(2), (4) Date: May 18, 2006

(87) PCT Pub. No.: WO2005/049557

PCT Pub. Date: Jun. 2, 2005

(65) Prior Publication Data

US 2007/0037260 A1 Feb. 15, 2007

(30) Foreign Application Priority Data

Nov. 18, 2003 (JP) ............... 2003-387965
Jun. 11, 2004 (JP) ............... 2004-173696
Jun. 15, 2004 (JP) ............... 2004-176623
Jun. 23, 2004 (JP) ............... 2004-184595
Jun. 23, 2004 (JP) ............... 2004-184596

(51) Int. Cl.
*C12P 13/12* (2006.01)

(52) U.S. Cl. .................................. 435/113

(58) Field of Classification Search ............ None
See application file for complete search history.

(56) References Cited

U.S. PATENT DOCUMENTS 6,372,912 B1 4/2002 Doring et al.
7,208,631 B2 * 4/2007 Higuchi et al. ............ 564/193
2006/0287398 A1 12/2006 Higuchi et al.

2007/0112216 A1 5/2007 Kotthaus et al.

FOREIGN PATENT DOCUMENTS

| EP | 1059288 A | 12/2000 |
|---|---|---|
| JP | S54-106488 A | 8/1979 |
| JP | 2000-309572 A | 11/2000 |
| JP | 2002-034593 A | 2/2002 |
| JP | 2002-315597 A | 10/2002 |
| JP | 2002-348282 A | 12/2002 |
| WO | 2004/090152 A | 10/2004 |
| WO | 2004/092119 A | 10/2004 |
| WO | 2005/061469 A | 7/2005 |

OTHER PUBLICATIONS

Woodward, G. E., et al., "The reaction of cysteine with acetone. A note on the titration of cysteine by the acetone-hydrochloric acid method of Lindstrom-Lang", Journal of the American Chemical Society, Washington, USA, vol. 59, No. 9, 1937, pp. 1690-1694.
Database, Derwent Publications Ltd., London, GB; AN 2003-620677, JP 2002 348282 A (Mitsubishi Gas Chem. Co. Inc.) Dec. 4, 2002 (Abstract).
Database, Derwent Publications Ltd., Lond, GB; AN 1979-70962B, JP 54 106488 A (Taisho Pharm Co., Ltd. Aug. 21, 1979. (Abstract).
Jeanguenat, Andre, et al., "Stereoselective Chain Elongation at C-3 of cysteine through 2,3-Dihydrothiazoles, without Racemization. Preparation of 2-Amino-5-hydroxy-3-mercapto-alkanioc Acid Derivatives" Journal of the Chemical Society, Perkins Trans., 1, pp. 2291-2298, 1991.

* cited by examiner

*Primary Examiner*—Herbert J. Lilling
(74) *Attorney, Agent, or Firm*—Kendrew H. Colton; Fitch, Even, Tabin & Flannery (57) ABSTRACT

There is provided a process for producing an optically active 2-alkylcysteine or a salt thereof, characterized by allowing cells of microorganism or treated products thereof having an activity of stereoselective hydrolysis of the amide bond of a 2-alkyl-L-cysteinamide or a salt thereof to act on a 2-alkyl-cysteinamide consisting of a mixture of D- and L-isomers or a salt thereof; and allowing the obtained 2-alkyl-L-cysteine and 2-alkyl-D-cysteinamide to react with an aldehyde or a ketone, or an acetal or ketal thereof, so as to derive therefrom a 4-alkylthiazolidine-4-carboxylic acid or a salt thereof and a 4-alkylthiazolidine-4-carboxamide or a salt thereof, thereby efficiently separating and obtaining a 2-alkyl-L-cysteine or a salt thereof, or a 2-alkyl-D-cysteine or a salt thereof. There is also provided a process for producing a 4-alkylthiazolidine-4-carboxylic acid or a salt thereof from the 2-alkylcysteine or a salt thereof.

12 Claims, 2 Drawing Sheets

PROCESS FOR PRODUCING OPTICALLY ACTIVE 2-ALKYCYSTEINE, DERIVATIVE THEREOF, AND PROCESSES FOR PRODUCTION

This Application is the National Phase of International Application No. PCT/JP2004/017140 filed Nov. 18, 2004, which designated the U.S. and was not published under PCT Article 21(2) in English, and this application claims, via the aforesaid International Application, the foreign priority benefit of and claims the priority from Japanese Application No. 2003-387965, filed Nov. 18, 2003, Japanese Application No. 2004-173696, filed Jun. 11, 2004, Japanese Application No. 2004-176623, Jun. 15, 2004, Japanese Application No. 2004-184595, filed Jun. 23, 2004, and Japanese Application No. 2004-184596, filed Jun. 23, 2004, the complete disclosures of the aforesaid PCT application and the aforesaid Japanese applications are incorporated herein by reference.

TECHNICAL FIELD

The present invention relates to a process for producing an optically active 2-alkylcysteine represented by the later-shown general formula (2) or (7) or a salt thereof from a 2-alkylcysteinamide represented by the later-shown general formula (1) or a salt thereof. More specifically, it relates to a process for producing an optically active 2-alkylcysteine or a salt thereof, which is characterized in that the process comprises allowing cells of microorganism or treated products thereof having an activity of stereoselective hydrolysis of the amide bond of a 2-alkyl-L-cysteinamide or a salt thereof to act on a 2-alkylcysteinamide consisting of a mixture of D- and L-isomers represented by the later-shown general formula (1) or a salt thereof, and allowing the obtained 2-alkyl-L-cysteine and 2-alkyl-D-cysteinamide to react with an aldehyde or ketone represented by the general formula (4), or an acetal or ketal thereof, so as to derive therefrom a 4-alkylthiazolidine-4-carboxylic acid represented by the general formula (5) or a salt thereof and a 4-alkylthiazolidine-4-carboxamide represented by the general formula (6) or a salt thereof, thereby efficiently separating and obtaining a 2-alkyl-L-cysteine represented by the general formula (2) or a salt thereof, or a 2-alkyl-D-cysteine represented by the general formula (7) or a salt thereof.

In addition, the present invention also relates to a 4-alkylthiazolidine-4-carboxylic acid represented by the later-shown general formula (8) or a salt thereof; optically active 4-alkylthiazolidine-4-carboxylic acids represented by the later-shown general formulas (5) and (9) or salts thereof; and a process for producing them from a 2-alkylcysteine represented by the later-shown general formula (10), or from an optically active 2-alkylcysteine represented by later-shown the general formula (2) or (7).

Such an optically active 2-alkylcysteine or a salt thereof, a 4-alkylthiazolidine-4-carboxylic acid or a salt thereof, and an optically active 4-alkylthiazolidine-4-carboxylic acid or a salt thereof, are important substances used as intermediates for production of various industrial chemicals, agricultural chemicals, and pharmaceuticals.

BACKGROUND ART

Conventionally, there has been known a production process of an optically active 2-alkylcysteine, in which an optically active cysteine methyl ester as a starting material is cyclized with pivalaldehyde and protected with formaldehyde, and then methylated with a lithium reagent and methyl iodide, followed by ring-opening with hydrochloric acid and deprotection so as to obtain an optically active 2-methylcysteine in the form of hydrochloride (see Patent Document 1 and Non-Patent Document 1, for example). The obtained optically active 2-methylcysteine can be esterified by addition of acetyl chloride thereto in alcohol. However, this process requires the optically active substance to be a starting material that is expensive. In addition, this process requires a large number of complicated steps, and also requires expensive reagents. Thus, it is hardly said that this is an industrially excellent process.

Further, there has been reported another process of producing an optically active 2-alkylcysteine in which an L-cysteine ethyl ester as a starting material is cyclized with a nitrile compound and methylated with a methylating agent such as methyl iodide to obtain a 4-alkylthiazoline-4-carboxylic acid ester, and the obtained ester is converted to a racemic body of a 4-methylthiazoline-4-carboxylic acid by a basic hydrolysis and then subjected to optical resolution using a basic optical resolution agent such as phenethylamine, or the 4-alkylthiazoline-4-carboxylic acid ester is subjected to a stereoselective hydrolysis using microorganisms to perform optical resolution and then hydrolyzed, to yield an optically active 2-methylcysteine (see Patent Documents 2 and 3, for example). Although this process uses an optically active substance as a raw material, it yields an intermediate of racemic body during the reaction, and requires the optical resolution to be carried out again. Hence, this process includes complicated steps, and it is hardly said that this is an industrially excellent process.

Meanwhile, it is anticipated that 4-alkylthiazolidine-4-carboxylic acids represented by the later-shown general formulas (5), (8), and (9) or salts thereof can be widely used as production materials such as for various industrial chemicals, agricultural chemicals, and pharmaceuticals. Thus, these substances are extremely useful in the industry. In addition, these 4-alkylthiazolidine-4-carboxylic acids or salts thereof can easily undergo a ring-opening reaction at their S—C—N site so as to be derivatized to 2-alkylcysteins. Such a 2-alkylcystein is also useful as a material for producing various industrial chemicals, agricultural chemicals, and pharmaceuticals. However, since the 2-alkylcystein has plural functional groups with high reactivity such as a mercapto group and amino group, it cannot be used as a substrate for carrying out a reaction for yielding a desired derivative selectively. In contrast, the 4-alkylthiazolidine-4-carboxylic acid or a salt thereof can be led to a 2-alkylcysteine derivative of interest by effecting a reaction for obtaining a derivative of a target substance followed by the ring-opening reaction. Thus, the 4-alkylthiazolidine-4-carboxylic acid or a salt thereof is a substance that is important also as a 2-alkylcysteine equivalent.

Although the 4-alkylthiazolidine-4-carboxylic acid or a salt thereof is a compound extremely useful as a reaction material for organic synthesis as stated above, a production process thereof has not yet been known. On the other hand, 5,5-dimethylthiazolidine-4-carboxylic acid has previously been known as a derivative of the 4-alkylthiazolidine-4-carboxylic acid (see Non-Patent Document 2, for example). However, it has a thiazolidine ring which is too rigid to open the ring and return it to a penicillamine derivative. There has also been known an ester or the like of the 4-alkylthiazolidine-4-carboxylic acid, in which nitrogen on the thiazolidine ring is protected by a formyl group (see Patent Document 1 and Non-Patent Document 1, for example). However, since the thiazolidine ring is opened at the same time as deformylation, it is impossible to obtain the 4-alkylthiazolidine-4-carboxylic acids represented by the later-shown general formulas (5), (8), and (9) or the salts thereof in this process.

Patent Document 1: U.S. Pat. No. 6,403,830
Patent Document 2: Japanese Patent Laid-Open No. 2003-201284
Patent Document 3: EP Patent No. 1302467
Non-Patent Document 1: Gerald Pattenden, Stephen M. Thom and Martin F. Jones, Tetrahedron, Vol. 49, No. 10, pp. 2131-2138, 1993
Non-Patent Document 2: Justus Liebigs Ann. Chem. (1966), 697, 140-157

DISCLOSURE OF THE INVENTION

Problems that is to be Solved by the Invention

It is an object of the present invention to solve the aforementioned problems of conventional techniques, and to provide a process for inexpensively producing a high-quality optically active 2-alkylcysteine or a salt thereof which is important as an intermediate for production of various industrial chemicals, agricultural chemicals and pharmaceuticals, and also provide a process for producing a 4-alkylthiazolidine-4-carboxylic acid or a salt thereof which is also important as well as their optically active ones at low cost and high quality.

Means that Solve the Problems

The present inventors have conducted intensive studies regarding a process for producing an optically active 2-alkylcysteine at low cost and high quality. As a result, the present invention provides a process for producing an optically active 2-alkyl-L-cystein or a salt thereof from a 2-alkylcysteinamide or a salt thereof, which is characterized in that the process comprises allowing cells of microorganism or a treated product thereof having an activity of stereoselective hydrolysis of the amide bond of a 2-alkyl-L-cysteinamide or a salt thereof to act on a 2-alkylcysteinamide consisting of a mixture of D- and L-isomers represented by the following general formula (1) or a salt thereof so as to selectively generate a 2-alkyl-L-cysteine or a salt thereof; allowing the mixture to react with an aldehyde or ketone represented by the general formula (4), or an acetal or ketal thereof so as to derive therefrom a 4-alkylthiazolidine-4-carboxylic acid represented by the general formula (5) or a salt thereof and a 4-alkylthiazolidine-4-carboxamide represented by the general formula (6) or a salt thereof, respectively; separating the 4-alkylthiazolidine-4-carboxylic acid represented by the general formula (5) or salt thereof from the mixture thereof; and hydrolyzing it for ring-opening to yield an optically active 2-alkyl-L-cysteine represented by the general formula (2) or a salt thereof, where in the general formulas (1), (2), (3), (5) and (6), R represents a $C_{1-4}$ lower alkyl; and in the general formulas (4), (5) and (6), each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen.

In a preferred embodiment, R represents methyl. In another preferred embodiment, $R_1$ and $R_2$ both represent methyl.

According to another aspect of the present invention, there is provided a process for producing an optically active 2-alkyl-D-cystein or a salt thereof from a 2-alkylcysteinamide or a salt thereof, which is characterized in that the process comprises allowing cells of microorganism or a treated product thereof having an activity of stereoselective hydrolysis of the amide bond of a 2-alkyl-L-cysteinamide or a salt thereof to act on a 2-alkylcysteinamide represented by the general formula (1) or a salt thereof so as to generate a 2-alkyl-L-cysteine represented by the general formula (2) or a salt thereof; allowing the generated 2-alkyl-L-cysteine or salt thereof and an unreacted 2-alkyl-D-cysteinamide represented by the general formula (3) or a salt thereof to react with an aldehyde or ketone represented by the general formula (4), or an acetal or ketal thereof so as to derive therefrom a 4-alkylthiazolidine-4-carboxylic acid represented by the general formula (5) or a salt thereof and a 4-alkylthiazolidine-4-carboxamide represented by the general formula (6) or a salt thereof, respectively; separating the 4-alkylthiazolidine-4-carboxamide represented by the general formula (6) or salt thereof from the mixture thereof; and hydrolyzing it for ring-opening and amide hydrolysis to yield an optically active 2-alkyl-D-cysteine represented by the general formula (7) or a salt thereof, -continued where in the general formulas (1), (2), (3), (5), (6) and (7), R represents a $C_{1-4}$ lower alkyl; and in the general formulas (4), (5) and (6), each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen.

In a preferred embodiment, R represents methyl. In another preferred embodiment, $R_1$ and $R_2$ both represent methyl.

The above described processes for producing an optically active 2-alkylcysteine is convenient in that a 2-alkylcysteinamide as a mixture of D- and L-isomers can be used as a raw material which is readily available, so that optically active 2-alkylcysteines that are important intermediates for production of various industrial chemicals, agricultural chemicals, pharmaceuticals, and others can be produced efficiently at high quality. In addition, the above described production processes are also convenient in that the thus obtained optically active 2-alkylcysteines can further be esterified, so that optically active 2-alkylcysteine esters that are important intermediates for production of various industrial chemicals, agricultural chemicals, pharmaceuticals, and others, can be produced efficiently at high quality.

The above described processes for producing an optically active 2-alkylcysteine comprises a step in which a 2-alkyl-L-cysteine represented by the general formula (2) which is generated as a result of a biochemical asymmetric hydrolysis of the 2-alkylcysteinamide represented by the general formula (1) and an unreacted 2-alkyl-D-cysteinamide represented by the general formula (3), are allowed to react with an aldehyde or ketone represented by the general formula (4), or an acetal or ketal thereof, so as to derive therefrom a 4-alkylthiazolidine-4-carboxylic acid represented by the general formula (5) and a 4-alkylthiazolidine-4-carboxamide represented by the general formula (6), respectively. Thus, it becomes possible to efficiently separate each substance by a simple solid-liquid separation means. The thus obtained 4-alkylthiazolidine-4-carboxylic acid represented by the general formula (5) and 4-alkylthiazolidine-4-carboxamide represented by the general formula (6) can be hydrolyzed to yield an optically active 2-alkyl-L-cysteine and an optically active 2-alkyl-D-cysteine, respectively. In this production process, there are differences in physico-chemical properties such as solubility in water and various types of organic solvents and distribution coefficients, between the compounds represented by the general formulas (5) and (6) greater than between the compounds represented by the general formulas (1) and (2). Accordingly, this production process enables efficient separation of the compounds at high purity.

The aforementioned 2-alkyl-L-cysteine represented by the general formula (2) or a salt thereof, the aforementioned 2-alkyl-D-cysteine represented by the general formula (7) or a salt thereof, and the 2-alkylcysteine represented by the general formula (10) or a salt thereof that is a mixture of the above compounds, can be allowed to react with an aldehyde or ketone represented by the following general formula (4), or an acetal or ketal thereof, so as to derive therefrom a 4-alkylthiazolidine-4-carboxylic acid or a salt thereof, or optically active substances thereof. The obtained 4-alkylthiazolidine-4-carboxylic acid or a salt thereof, or optically active substances thereof, are novel compounds.

where in the general formulas (2), (5), (7), (8), (9) and (10), R represents a $C_{1-4}$ lower alkyl; and in the general formulas (4), (5), (8) and (9), each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen.

In a preferred embodiment, R represents methyl in the above described formulas (2), (5), (7), (8), (9), and (10). In another preferred embodiment, $R_1$ and $R_2$ both represent methyl in the above described formulas (4), (5), (8), and (9).

Thus, the present invention provides a process for producing a 4-alkylthiazolidine-4-carboxylic acid or a salt thereof, or an optically active substance thereof represented by the general formula (5), (8), or (9):

(8)

where in the general formula (8), R represents a $C_{1-4}$ lower alkyl; and each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen, and (5)

(9)

where in the general formulas (5) and (9), R represents a $C_{1-4}$ lower alkyl; and each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen.

In a preferred embodiment, R represents methyl in the above described formulas (5), (8), and (9). In another preferred embodiment, $R_1$ and $R_2$ both represent methyl in the above described formulas (5), (8), and (9).

Furthermore, the present invention provides 4-alkylthiazolidine-4-carboxylic acids represented by the above general formulas (8), (5), and (9), or salts thereof, which are anticipated to be widely used as production materials such as for various industrial chemicals, agricultural chemicals and pharmaceuticals, and thus are industrially extremely useful.

BEST MODE FOR CARRYING OUT THE INVENTION

Figure 1:
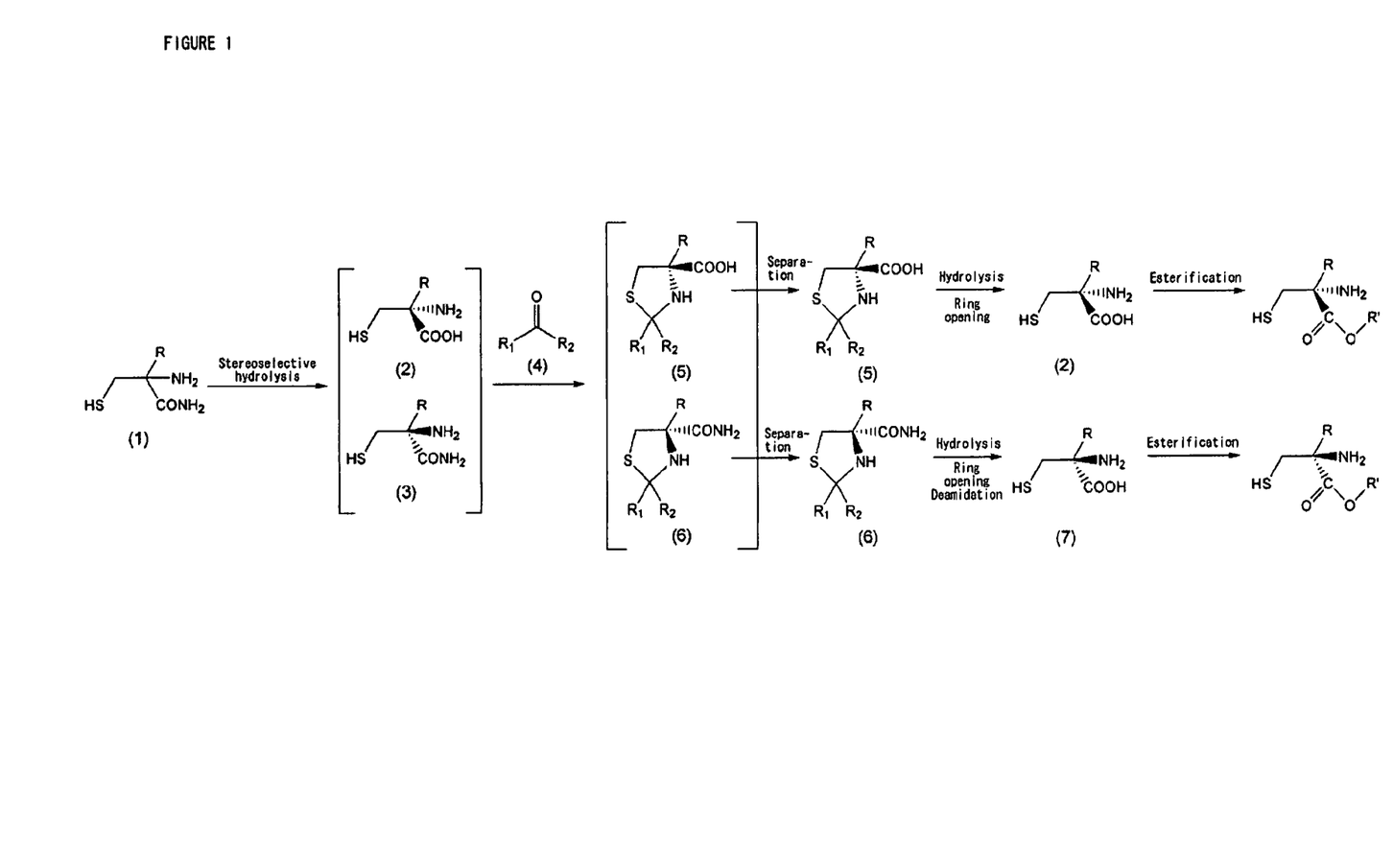
FIG. 1 is a schematic view showing the synthesis scheme of an optically active 2-alkylcysteinamide by use of a 2-alkylcysteinamide as a raw material according to the present invention.
Figure 2:
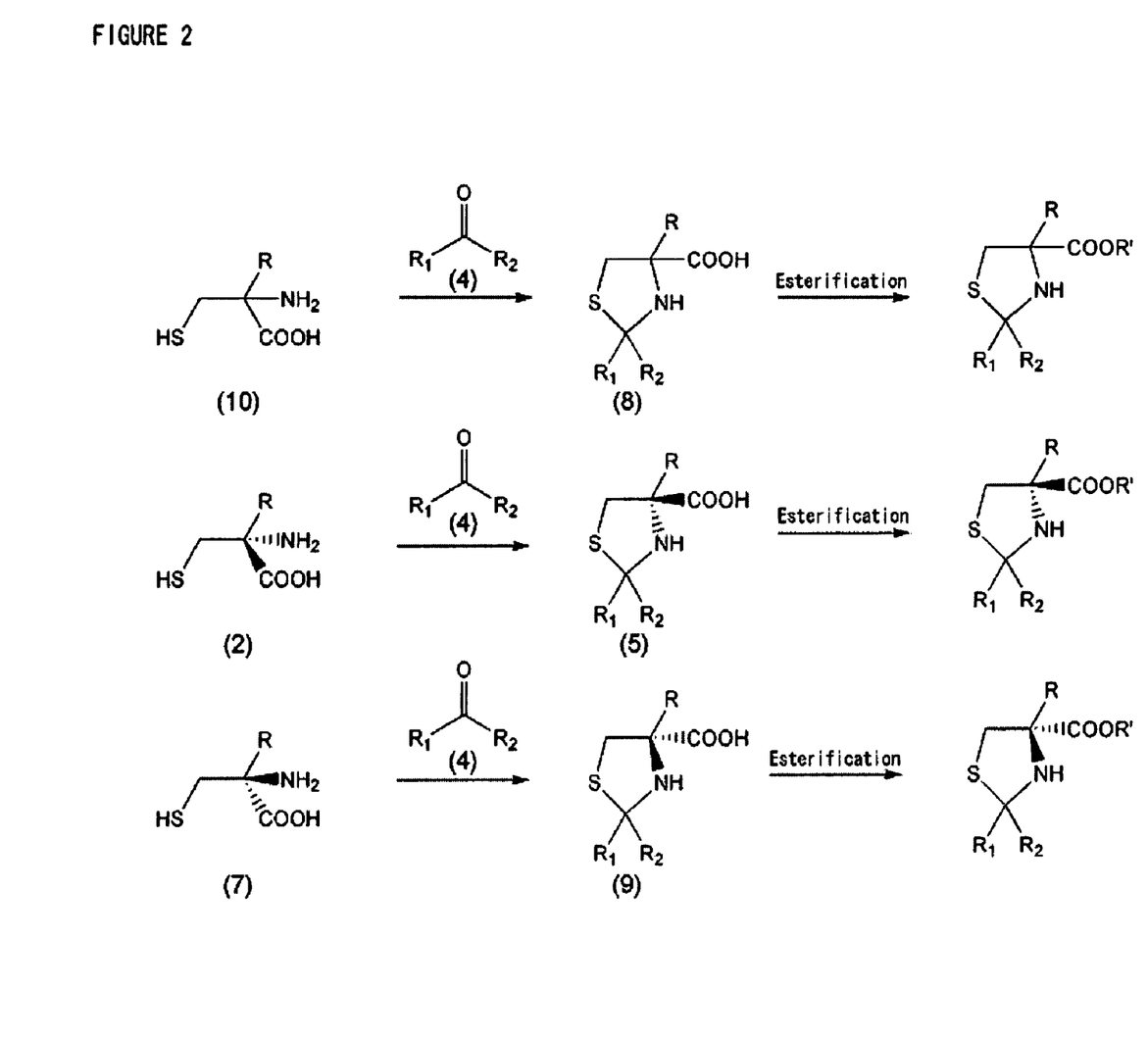
FIG. 2 is a schematic view showing the synthesis scheme of a 4-alkylthiazolidine-4-carboxylic acid by use of a 2-alkylcysteine as a raw material according to the present invention.

A scheme of the production process of the present invention is schematically shown in FIGS. 1 and 2. The present invention will be described in detail below with reference to these drawings.

(A-1) 2-alkylcysteinamide represented by the general formula (1) or salt thereof In the general formula (1) representing a 2-alkylcysteinamide or a salt thereof used as a raw material in the present invention, R is not particularly limited, as long as it is a $C_{1-4}$ lower alkyl. Preferred examples of such R include linear or branched lower alkyl such as methyl, ethyl, propyl, isopropyl, butyl, isobutyl, sec-butyl, and tert-butyl. Of these, methyl is particularly preferable. The 2-alkylcysteinamide may also be used in a form of a salt such as hydrochloride, sulfate and acetate, as well as in a free form.

A process for producing such a 2-alkylcysteinamide is not particularly limited. For example, a 2-alkylcysteinamide can be obtained from a 4-alkylthiazolidine-4-carboxamide represented by the following general formula (11) or a salt thereof:

(11)

Such a 4-alkylthiazolidine-4-carboxamide or a salt thereof can be produced as described below by use of a method described in a literature, Justus Liebigs Ann. Chem. (1966), 697, 140-157, etc.

1) A halogenated methyl alkyl ketone represented by the formula (12) shown below (wherein X represents a halogenated methyl group) and a carbonyl compound represented by the formula (13) shown below or an acetal or ketal thereof are allowed to react with sodium hydrosulfide and ammonia, so as to obtain a thiazoline compound represented by the formula (14) shown below.

2) HCN is added to the obtained thiazoline represented by the formula (14) to obtain a nitrile represented by the formula (15) shown below.

3) The nitrile represented by the formula (15) is hydrolyzed with an acid catalyst to obtain a 4-alkylthiazolidine-4-carboxamide represented by the general formula (11) or its salt which is particularly shown below by the formula (11').

The 2-alkylcysteinamide represented by the general formula (1) or a salt thereof can be produced by partially hydrolyzing the 4-alkylthiazolidine-4-carboxamide represented by the general formula (11) or a salt thereof. When the 4-alkylthiazolidine-4-carboxamide represented by the general formula (11) or a salt thereof is dissolved in pure water or a polar organic solvent containing water in an equivalent or more amount and heated, a hydrolytic ring-opening reaction progresses. This hydrolytic reaction can be accelerated by addition of an acid catalyst. However, when an excessive amount of acid is present, a large amount of 2-alkylcysteine resulting from a further hydrolysis of the 2-alkylcysteinamide represented by the general formula (1) is unfavorably produced as a by-product. Thus, an acid catalyst is used at a ratio on equivalent basis of preferably between 0.5 to 1.3, more preferably from 0.8 to 1.1, and most preferably 1 relative to the thiazolidine carboxamide represented by the general formula (11). Alternatively, the 2-alkylcysteinamide of interest represented by the general formula (1) can favorably be obtained by isolating and purifying the neutral salt represented by the formula (11') which consists of the thiazolidine carboxamide and an acid, and then heating it to reflux in pure water or a polar organic solvent containing water in an equivalent or more amount.

It is to be noted that R, $R_1$, and $R_2$ in the above formulas (12), (13), (14), (15), (11), and (11') have the same meanings as those in the above general formulas (1) and (4).

Types of the acid used as a catalyst are not particularly limited, as long as they are commonly used. Examples of the acid include inorganic acids such as hydrochloric acid, sulfuric acid and phosphoric acid, and organic acids such as formic acid and acetic acid. Of these, inorganic acids such as hydrochloric acid and sulfuric acid are preferably used because of high reaction rate or favorable operability during purification. In this instance, the carbonyl compound represented by the formula (13) is dissociated as a result of the hydrolysis. By conducting the reaction with the carbonyl compound being removed from the reaction system by such an operation as distillation, the reaction can proceed more efficiently. The reaction quantitatively progresses, and only by eliminating the dissociated carbonyl compound represented by the formula (13) and a reaction solvent, the 2-alkylcysteinamide of interest represented by the general formula (1) or a salt thereof can be obtained at high yield and at high purity.

(A-2) stereoselective hydrolysis of 2-alkylcysteinamide represented by general formula (1) or salt thereof In the present invention, cells of microorganism or a treated product thereof having an activity of biochemical asymmetric hydrolysis of the amide bond of a 2-alkyl-L-cysteinamide or a salt thereof is allowed to act on a 2-alkylcysteinamide consisting of a mixture of D- and L-isomers represented by the general formula (1) or a salt thereof, so as to selectively generate a 2-alkyl-L-cysteine or a salt thereof. Hence, a mixture is formed which consists of the 2-alkyl-L-cysteine represented by the general formula (2) or a salt thereof and a 2-alkyl-D-cysteinamide represented by the general formula (3) or a salt thereof.

Types of microorganism used herein are not particularly limited, as long as they have an activity of stereoselective hydrolysis of the amide bond of a 2-alkyl-L-cysteinamide or a salt thereof to generate a 2-alkyl-L-cysteine or a salt thereof. Examples of the microorganism include those belonging to the genus *Xanthobacter*, the genus *Protaminobacter*, and the genus *Mycoplana*. Specific examples may include *Xanthobacter flavus* NCIB 10071, *Protaminobacter alboflavus* ATCC8458, *Mycoplana ramose* NCIB9440, and *Mycoplana dimorpha* ATCC4279, but examples are not limited thereto. In addition, both mutants induced from these microorganisms by artificial mutation procedures, and recombinants induced by genetic engineering procedures such as cell fusion and gene recombination, can also be used in the present invention, as long as they have the aforementioned ability.

These microorganisms are generally cultured in a medium which contain carbon sources and nitrogen sources that can be generally assimilated, inorganic salts essential for each microorganism, nutrients, etc. The pH of such a medium is generally between 4 and 10, and the culture temperature is generally between 20° C. and 50° C.; however, such culture conditions may optionally be determined depending on the growth properties of microorganisms to be used. The culture is aerobically carried out for 1 day to 1 week. The thus cultured microorganism can be used for the reaction in a form of intact cells or a processed product of intact cells, including a culture solution, an isolated cell mass, a crushed cell mass product, and a purified enzyme. Moreover, such a cell or enzyme may also be immobilized in use according to an ordinary method.

Conditions for the biochemical asymmetric hydrolysis of the 2-alkylcysteinamide or a salt thereof are as follows. The concentration of the 2-alkylcysteinamide or a salt thereof used as a substrate is preferably between 0.1% and 40% by weight, and more preferably between 0.5% and 20% by weight. When the concentration of the substrate is less than 0.1% by weight, the volume of a reaction solution simply increases, and thus it becomes disadvantageous in terms of productivity. In contrast, when the substrate concentration exceeds 40% by weight, substrate inhibition takes place, and thus it becomes disadvantageous in terms of productivity per the cell or treated product thereof; moreover, there may be cases where the 2-alkyl-L-cysteine or a salt thereof as a reaction product is precipitated at the midpoint of the reaction, and thus, it becomes disadvantageous in that this may cause losses when centrifugation or separation by filtration of cells or treated products thereof is performed.

The amount of the cells of microorganism or treated products thereof to be used is such that the ratio on dry weight basis of cells of microorganism used as a raw material is preferably between 0.0001 and 3, and more preferably between 0.001 and 1 relative to the 2-alkylcysteinamide or a salt thereof as a substrate. When such a weight ratio is less than 0.0001, it causes a slow reaction rate, and thus a long period of time is required for the operation. In contrast, when it exceeds 3, the reaction time is shortened, but it cannot be said that this is efficient in terms of usage of cells of microorganisms; and moreover, this is industrially disadvantageous in that much work is required for separation of the cells or treated products thereof after the reaction. When the reaction solution contains a high concentration of the 2-alkylcysteinamide as a raw material, the above ratio of cells of microorganism or treated products thereof to be used may be appropriately determined as far as it is no more than the upper limit of the above preferred range, i.e., 3 or less and allows the reaction to progress favorably.

The reaction temperature is preferably between 10° C. and 70° C., and more preferably between 20° C. and 40° C. When the reaction temperature is lower than 10° C., it causes a slow reaction rate, and thus a long period of time is disadvantageously required for the operation. In contrast, when the reaction temperature exceeds 70° C., the enzyme catalytic activity of cells or treated products thereof decreases due to deactivation, and non-enzymatic decomposition of 2-alkyl-D-cysteinamide also takes place. Thus, this is disadvantageous in terms of reaction yield and selectivity. In addition, a large amount of energy is required for heating and cooling the reaction solution between production steps, and thus this is disadvantageous in terms of cost.

The reaction solution is preferably an aqueous solution of pH 4 to pH 13, more preferably of pH 5 to pH 10, and particularly preferably of pH 7 and pH 9 ranging from neutral conditions to relatively moderate basic conditions. When the pH is less than 4, the catalytic activity of cells of microorganism or treated products thereof decreases. When the pH exceeds 13, the catalytic activity also decreases; and moreover, 2-alkyl-D-cysteinamide or a salt thereof, 2-alkyl-L-cysteinamide or a salt thereof and a 2-alkyl-L-cysteine or a salt thereof as a generated product that are contained in the reaction solution form a disulfide bond, thereby dimerizing unfavorably. Further, a non-enzymatic hydrolysis of the 2-alkyl-D-cysteinamide or a salt thereof takes place. This is not preferable either. In order to adjust the pH of the reaction solution, inorganic bases such as sodium hydroxide and potassium hydroxide, ammonia, and so on may be used. Also, a buffer solution in which other substances are dissolved may be used.

For the reaction, metal ions such as Mg, Cu, Zn, Fe, Mn, Ni and Co may also be added as activators for enzyme catalysts. The amount of such metal ions to be added depends on types of strains of cultured microorganisms or types of metal ions to be added. The asymmetric hydrolysis rate can be improved by adding metal ions at a concentration preferably between 1 and 50 ppm, and more preferably between 5 and 20 ppm. When divalent Mn ions are added at a concentration between 5 and 20 ppm for example, the reaction rate can significantly be improved, and it is 2 to 5 times higher than a case where no such metal ions are added. It is to be noted that cells of microorganism or treated products thereof that have been used for a biochemical asymmetric hydrolysis can be recovered by centrifugation, filtration or the like after they have been used for the enzymatic reaction, and they can be reused as an enzyme catalyst for the asymmetric hydrolysis.

The 2-alkylcysteinamide or a salt thereof as a raw material, or the reaction products thereof, namely, the 2-alkyl-L-cysteine or a salt thereof or a 2-alkyl-D-cysteinamide or a salt thereof, has a mercapto group in a structure thereof. Thus, these compounds are likely to be oxidized. Accordingly, if these compounds are left in the presence of oxygen, they become a dimeric disulfide (2,2'-dialkylcystine). In order to prevent this, a series of production steps ranging from an asymmetric hydrolysis using cells of microorganism or treated products thereof through concentration and/or purification are preferably carried out in an atmosphere of inert gas such as nitrogen and argon, or alternatively carried out in the co-existence of a reducing substance such as 2-mercaptoethanol in the reaction system. Moreover, if all solvents used for the reaction are degased before the reaction, the reaction can preferably progress without generation of by-products.

After the reaction, cells of microorganisms are removed from the reaction solution by a common solid-liquid separation means such as centrifugation and a filtration membrane. Further, it is more preferable that the remaining organic matters derived from the microorganisms are eliminated by ultrafiltration or an adsorbent such as activated carbon. Subsequently, the reaction solution is concentrated by distilling water away. The obtained concentrate is used as a raw material for the subsequent thiazolidine cyclization reaction.

(A-3) cyclization reaction of mixture consisting of 2-alkyl-L-cysteine represented by the general formula (2) or salt thereof and 2-alkyl-d-cysteinamide represented by the general formula (3) or salt thereof In the present invention, the 2-alkyl-L-cysteine represented by the general formula (2) or a salt thereof that has been generated as a result of the biochemical asymmetric hydrolysis of the 2-alkylcysteinamide represented by the general formula (1) or a salt thereof, and an unreacted 2-alkyl-D-cysteinamide represented by the general formula (3) or a salt thereof, are allowed to react with an aldehyde or ketone represented by the general formula (4), or an acetal or ketal thereof, so as to derive therefrom the 4-alkylthiazolidine-4-carboxylic acid represented by the general formula (5) and the 4-alkylthiazolidine-4-carboxamide represented by the general formula (6), respectively.

Each of $R_1$ and $R_2$ in the general formula (4) representing the aldehyde or ketone used herein, is not particularly limited as long as they independently represent hydrogen (provided that $R_1$ and $R_2$ do not simultaneously represent hydrogen) or a $C_{1-4}$ lower alkyl, or both $R_1$ and $R_2$ bind to each other to form a 5- to 8-membered alicyclic structure. Preferred examples of the $C_{1-4}$ lower alkyl include linear or branched lower alkyl such as methyl, ethyl, propyl, isopropyl, butyl, isobutyl, sec-butyl and t-butyl. Preferred examples of the alicyclic structure include alicyclic rings such as a cyclobutane ring, a cyclopentane ring and a cyclohexane ring. Among others, a cyclopentane ring and a cyclohexane ring are particularly preferable. Of these, a case where both $R_1$ and $R_2$ represent methyl is particularly preferable. Specific examples of such compounds include acetone, methyl ethyl ketone, diethyl ketone, 5-nonanone, acetaldehyde, cyclopentanone and cyclohexanone. In particular, acetone and cyclopentanone are preferably used. Further, acetone is most preferably used.

The acetal or ketal of an aldehyde or ketone includes those represented by the following general formula (4'):

(4')

wherein each of $R_1$ and $R_2$ independently represents hydrogen or a $C_{1-4}$ lower alkyl, or both $R_1$ and $R_2$ bind to each other to form a 5- to 8-membered alicyclic structure, provided that $R_1$ and $R_2$ do not simultaneously represent hydrogen; and each of $R_3$ and $R_4$ independently represents $C_{1-3}$ lower alkyl, or both $R_3$ and $R_4$ bind to each other to form a 5- to 8-membered alicyclic structure.

Preferred examples of the $C_{1-4}$ lower alkyl represented by $R_1$ and $R_2$ in the general formula (4') include a linear or branched lower alkyl such as a methyl, ethyl, propyl, isopropyl, butyl, isobutyl, sec-butyl and t-butyl. Preferred examples of the alicyclic structure include a cyclobutane ring, a cyclopentane ring, a cyclohexane ring and a cycloheptane ring. Among others, a cyclopentane ring and a cyclohexane ring are particularly preferable. Of these, a case where both $R_1$ and $R_2$ represent methyl is particularly preferable.

Examples of the $C_{1-3}$ lower alkyl represented by $R_3$ and $R_4$ in the general formula (4') include a linear or branched lower alkyl such as methyl, ethyl, propyl and isopropyl. Examples of the alicyclic structure include an ethylene acetal ring and a propylene acetal ring. Specific examples of such a compound include acetone dimethyl acetal, acetone ethylene acetal and cyclohexanone ethylene acetal. In particular, acetone dimethyl acetal is preferably used.

The cyclization reaction is preferably carried out in an organic solvent. Preferred examples of such an organic solvent include an aldehyde or ketone represented by the general formula (4) and an acetal or ketal thereof since they also act as a substrate for the reaction, and thus save the molecular species in the reaction system. Addition amount of the aldehyde or ketone, or the acetal or ketal thereof may be equimolar to or larger than the total amount of 2-alkyl-L-cysteine and 2-alkyl-D-cysteinamide that are subjected to thiazolidine cyclization, and has no particular upper limit. The larger the addition amount is, the faster the reaction speed is. Thus, from the viewpoint of economy, the upper limit is preferably set to be a concentration that provides a homogeneous solution. In this case, if the reaction substrate or reaction product still cannot be dissolved sufficiently to give a homogeneous reaction system, a solvent may be appropriately selected and used which maintains the system to be homogeneous even in a small addition amount but does not affect the reaction. Preferred examples of such a solvent include alcohols such as methanol and ethanol.

Further, the cyclization reaction is more preferably carried out while water generated as a result of the reaction is removed. The dehydration method is not particularly limited, but a Dean-Stark separator or a dehydrating agent such as a molecular sieve may be used. When a dehydrating agent is used, it is used preferably in an amount that provides a dehydrating capacity which is equimolar to or higher than, and preferably 1.2 times or higher than the amount of the water that will be generated. The reaction temperature is not particularly limited. The reaction progresses rapidly as the temperature elevates. Thus, it is generally preferable that the reaction be carried out at a reflux temperature.

The cyclization reaction may progress without catalysts. However, the reaction progresses more rapidly with addition of a small amount of a base. The base to be used is not particularly limited, but examples thereof include basic substances such as sodium hydroxide, tetramethylammonium hydroxide, ammonia and trimethylamine; and salts exhibiting basicity such as sodium carbonate. If the amount of such a base is excessive, the amount of acid is unfavorably increased that is necessary for neutralization in a post-treatment. Appropriately, the amount of the base is 5 times or less, and preferably 1 to 3 times the equivalent amount of the 2-alkylcysteinamide as a raw material.

(A-4) separation of optically active 4-alkylthiazolidine-4-carboxylic acid represented by the general formula (5) or salt thereof after cyclization reaction After completion of the cyclization reaction, solvents and volatile substances are removed from the reaction solution. Then, 4-alkylthiazolidine-4-carboxamide or a salt thereof is extracted as soluble matter from the obtained concentrate using an appropriate organic solvent such as alcohols. 4-alkylthiazolidine-4-carboxylic acid or a salt thereof that remains as insoluble matter is separated by filtration. The separated 4-alkylthiazolidine-4-carboxylic acid can be recrystallized using an appropriate organic solvent, so as to eliminate impurities such as proteins, nucleic acids and 4-alkylthiazolidine-4-carboxamide or a salt thereof. As an organic solvent used in this instance, a solvent may be selected as appropriate, which enables inorganic salts to be eliminated by filtration under heating and exhibits, upon aging of crystals, high solubility of proteins, nucleic acids and others that have been mixed in during the biochemical asymmetric hydrolysis whilst the 4-alkylthiazolidine-4-carboxylic acid of interest represented by the general formula (5) or salt thereof is hardly dissolved. For example, alcohols such as ethanol and butanol, and ethers such as tetrahydrofuran and dioxane, are preferably used.

(A-5) separation of optically active 4-alkylthiazolidine-4-carboxamide represented by the general formula (6) or salt thereof after cyclization reaction After completion of the cyclization reaction, solvents and volatile substances are removed from the reaction solution. Then, 4-alkylthiazolidine-4-carboxamide or a salt thereof is extracted as soluble matter from the obtained concentrate using an appropriate organic solvent such as alcohols. 4-alkylthiazolidine-4-carboxylic acid or a salt thereof that remains as insoluble matter is separated by filtration. The 4-alkylthiazolidine-4-carboxamide obtained as an extract solution is concentrated and dried using an evaporator or the like, and then washed with an appropriate organic solvent, so as to eliminate impurities such as proteins, nucleic acids and 4-alkylthiazolidine-4-carboxylic acid and a salt thereof. As an organic solvent used in this instance, there is no particular limitation, and a solvent may be selected as appropriate, which dissolves proteins, nucleic acids and others that have been mixed in during the biochemical asymmetric hydrolysis whilst the 4-alkylthiazolidine-4-carboxamide of interest represented by the general formula (6) or a salt thereof is hardly dissolved. For example, ketones such as acetone and cyclohexanone, and hydrocarbons such as hexane and cyclohexane, are preferably used.

Alternatively, after completion of the cyclization reaction, solvents and volatile substances may be removed from the reaction solution, and then the obtained concentrate may be dispersed in water. As a result, the 4-alkylthiazolidine-4-carboxylic acid as an L-isomer and a salt thereof are dissolved in the water, whereas the 4-alkylthiazolidine-4-carboxamide as a D-isomer represented by the general formula (6) or a salt thereof is precipitated as insoluble matter which is then filtrated and recovered. Thereafter, the 4-alkylthiazolidine-4-carboxamide or a salt thereof is washed with an appropriate organic solvent, so as to eliminate impurities such as proteins, nucleic acids and 4-alkylthiazolidine-4-carboxylic acid and a salt thereof. As an organic solvent used in this instance, there is no particular limitation, and a solvent may be selected as appropriate, which dissolves proteins, nucleic acids and others that have been mixed in during the biochemical asymmetric hydrolysis whilst the 4-alkylthiazolidine-4-carboxamide of interest represented by the general formula (6) or a salt thereof is hardly dissolved. For example, ketones such as acetone and cyclohexanone, and hydrocarbons such as hexane and cyclohexane, are preferably used.

(A-6) hydrolysis of 4-alkylthiazolidine-4-carboxylic Acid represented by the general formula (5) or salt thereof Hydrolytic ring-opening reaction of the thiazolidine ring proceeds by making the crystals of the 4-alkylthiazolidine-4-carboxylic acid represented by the general formula (5) or salt thereof as filtrated above into an aqueous solution, and then heating it to reflux. In this instance, the reaction rapidly progresses if it is conducted whilst taking a measure to eliminate the aldehyde or ketone represented by the general formula (4) which is being generated, for example, by way of the top of a reflux cooling tube to the outside of the reaction system. In addition, if an acid such as hydrochloric acid and sulfuric acid is used as a hydrolysis catalyst, the reaction more rapidly progresses. In this case, however, amino acids are obtained in the form of salts with such acids. The reaction time is different depending on the composition of a reaction solution or operation conditions. In general, when an aqueous solution of the 4-alkylthiazolidine-4-carboxylic acid or a salt thereof is heated to reflux while the generated aldehyde or ketone is eliminated to the outside of the reaction system, the reaction can be completed in approximately 1 to 6 hours.

The optically active 2-alkyl-L-cysteine represented by the general formula (2) or a salt thereof can be obtained by processing the reaction solution resulting from the aforementioned hydrolytic ring-opening reaction by means of, for example, concentration under reduced pressure. When aldehyde or ketone remains and cannot be distilled off, the reaction solution can be supplemented with a nonpolar organic solvent such as ether and methylene chloride so that the water layer can be separated and concentrated whilst aldehyde or ketone dissolved in and transferred to the upper layer is removed.

Thus, an optically active 2-alkyl-L-cysteine such as 2-methyl-L-cysteine and 2-ethyl-L-cysteine can be produced.

(A-7) hydrolysis of 4-alkylthiazolidine-4-carboxamide represented by the general formula (6) or salt thereof Ring-opening reaction and amide hydrolysis hydrolytically proceed by suspending the 4-alkylthiazolidine-4-carboxamide represented by the general formula (6) as filtrated above in water, and then heating it to reflux. As a result, 2-alkyl-D-cysteine is generated. In this instance, the reaction rapidly progresses if it is conducted whilst eliminating the aldehyde or ketone represented by the general formula (4), which is being generated, to the outside of the reaction system. In addition, if an acid such as hydrochloric acid and sulfuric acid is used as a hydrolysis catalyst, the reaction more rapidly progresses. In this case, however, amino acids are obtained in the form of salts with such acids.

After completion of the reaction, the reaction solution is supplemented with a nonpolar organic solvent such as diethyl ether and methylene chloride, followed by separation and washing so as to eliminate residual aldehyde or ketone. The resulting water layer is concentrated to yield an optically active 2-alkyl-D-cysteine represented by the general formula (7) or a salt thereof. When an acid such as hydrochloric acid and sulfuric acid is added as a hydrolysis catalyst, hydrolyzed amide may be converted into ammonium salts, and mixed into crystals. However, such ammonium salts can be eliminated by recrystallization of the obtained 2-alkyl-D-cysteine or by desalination thereof with an ion exchange resin or the like.

Thus, an optically active 2-alkyl-D-cysteine such as 2-methyl-D-cysteine and 2-ethyl-D-cysteine can be obtained.

(B-1) synthesis of 4-alkylthiazolidine-4-carboxylic acid or salt thereof using 2-aylcysteine or salt thereof as raw material As shown in FIG. 2, according to the present invention, the optically active 4-alkylthiazolidine-4-carboxylic acid represented by the general formula (5) or (9) or a salt thereof, or the 4-alkylthiazolidine-4-carboxylic acid represented by the general formula (8) or a salt thereof can be produced by allowing the optically active 2-alkylcysteine represented by the general formula (2) or (7) or a salt thereof, or the 2-alkylcysteine represented by the general formula (10) or a salt thereof, to react with the aldehyde or ketone represented by the general formula (4), or an acetal or ketal thereof.

In the general formulas (10), (2) and (7) representing the 2-alkylcysteine as raw materials, R may be a $C_{1-4}$ lower alkyl including, for example, methyl, ethyl, propyl, iso-propyl, butyl, iso-butyl, sec-butyl and tert-butyl. The 2-alkylcysteine represented by the general formulas (10), (2) and (7) used in the present invention, are not particularly limited in terms of production process and quality. For example, a racemic body obtained by the method involving hydrolysis of a corresponding 4-alkylthiazolidine-4-carboxamide derivative prepared by the method described in Justus Liebigs Ann. Chem. (1966), 697, 140-157; optically active substances obtained by the production processes described in U.S. Pat. No. 6,403,830 or Japanese Patent Laid-Open No. 2003-201284; and other substances, can be used. In addition, an optically active substance obtained by the method described in (A-6) or (A-7) above may also be used. The 2-alkylcysteine represented by the general formula (10) or a salt thereof may be either a mixture consisting of the 2-alkyl-L-cysteine represented by the general formula (2) or a salt thereof and the 2-alkyl-D-cysteine represented by the general formula (7) or a salt thereof, or a racemic mixture consisting of the above compounds in equal amounts.

As the aldehyde or ketone represented by the general formula (4), or an acetal or ketal thereof, the same compounds as described in (A-3) above may be used.

The aldehyde, ketone, acetal or ketal is used preferably in an excessive amount, that is, in an amount equimolar to or larger than the 2-alkylcysteine or a salt thereof, and particularly preferably in an amount of 2 times or more the equivalent amount thereof since the cyclization reaction between the aldehyde or ketone represented by the general formula (4) or the acetal or ketal represented by the general formula (4') and the 2-alkylcysteine or a salt thereof is an equilibrium reaction. The upper limit thereof is not particularly limited, but can be determined as appropriate, taking into consideration actual conditions of the reaction and economy.

The reaction between the 2-alkylcysteine represented by the general formula (10), (2) and (7) or a salt thereof, and the ketone or aldehyde represented by the general formula (4) or an acetal or ketal thereof, can be allowed to proceed by using such a ketone, aldehyde, acetal or ketal as a solvent, and heating the mixture. In this instance, the heating temperature is not particularly limited, but the reaction is preferably carried out at a boiling point of the prepared mixture solution under reflux. In addition, if the generated water is removed during the reaction, the reaction is promoted advantageously. The dehydration method is not particularly limited, but a Dean-Stark separator or a dehydrating agent such as a molecular sieve may be used. When a dehydrating agent is used, it is desirably used so as to remove water of an equivalent amount equal to or higher than, and preferably 1.2 times or higher than the 2-alkylcysteine as a raw material.

When the 2-alkylcysteine represented by the general formula (10), (2) and (7) or a salt thereof is low in solubility in the ketone or aldehyde represented by the general formula (4) or an acetal or ketal thereof, the reaction can be preferably carried out in coexistence of an organic solvent inert to the reaction so as to create a homogeneous system. A solvent used in this instance may be determined as appropriate, taking into consideration the solubility of the 2-alkylcysteine represented by the general formula (10), (2) and (7), and the solubility of the ketone or aldehyde represented by the general formula (4), or an acetal or ketal thereof. Thus, types of the solvent are not particularly limited. Considering such solubility, preferred examples of the solvent include polar solvents including alcohols such as methanol, ethanol and butanol, ethers such as diethyl ether and tetrahydrofuran, and amides such as dimethylformamide as well as mixed solvents thereof. Of these, alcohols such as methanol, ethanol and butanol are particularly preferable.

The reaction is more preferably carried out at a pH between pH 6.5 and pH 10. Thus, when the 2-alkylcysteine is in a form of a salt with a base such as a sodium salt, the reaction progresses rapidly without catalysts. However, when the 2-methylcysteine is used in a free form or a salt with an acid such as hydrochloride, a basic substance is preferably used as a catalyst. The basic substance used in this instance is not particularly limited, but an inorganic base such as sodium carbonate or an organic base such as triethylamine is preferably used, for example. Amount of the basic substance to be added in this instance is 0.05 times or more the mole amount of 2-alkylcysteine when the 2-alkylcysteine is in a free form. When the 2-alkylcysteine to be used is in a form of a salt with an acid, the addition amount of a basic substance can be increased by the amount corresponding to the amount of the acid. The pH of the reaction system preferably does not exceed pH 10. Also, the use of an excessive amount of the base requires a removal operation in a subsequent process, and thus is disadvantageous in terms of costs. The addition amount of the basic substance is preferably 0.5 to 3 times the 2-alkylcysteine on mole basis.

The 4-alkylthiazolidine-4-carboxylic acid represented by the general formula (8), (5) or (9), or a salt thereof, can be recovered after the reaction from the reaction solution by crystallization or extraction. The obtained 4-alkylthiazolidine-4-carboxylic acid or a salt thereof can appropriately be purified by common methods such as recrystallization which depend on physical properties thereof. The purified product can also be used as a material for synthesizing an ester form.

In the general formulas (8), (5) and (9) representing a 4-alkylthiazolidine-4-carboxylic acid or a salt thereof, R may be a $C_{1-4}$ lower alkyl. Examples of such a $C_{1-4}$ lower alkyl include linear or branched lower alkyl such as methyl, ethyl, propyl, iso-propyl, butyl, iso-butyl, sec-butyl and tert-butyl. In the general formulas (8), (5), (9), (4) and (4'), each of $R_1$ and $R_2$ independently represents hydrogen or a $C_{1-4}$ lower alkyl (provided that $R_1$ and $R_2$ do not simultaneously represent hydrogen), or $R_1$ and $R_2$ bind to each other to form a 5- to 8-membered alicyclic structure. Examples of the alkyl include methyl, ethyl, propyl, iso-propyl, butyl, iso-butyl, sec-butyl and tert-butyl. Examples of the alicyclic structure include a cyclopentane ring, a cyclohexane ring and a cyclooctane ring. As such alkyl, a case where both $R_1$ and $R_2$ represent methyl is particularly preferable. As such an alicyclic structure, a case where a cyclopentane ring structure is formed is particularly preferable.

The compounds represented by the general formula (8), (5) and (9), may form salts. Types of salts are not particularly limited, as long as they are practically acceptable. Examples of the salts may include salts with inorganic acids such as hydrochloric acid, sulfuric acid and phosphoric acid; salts with organic acids such as formic acid and acetic acid; salts with alkali metals such as sodium and potassium; salts with alkaline-earth metals such as magnesium and calcium; and ammonium salts such as ammonium and tetramethylammonium.

Specific examples of compounds produced by the process of the present invention may include a 4-alkylthiazolidine-4-carboxylic acid or a salt thereof, and an optically active substance thereof, such as a 2,2,4-trimethyl-(3)-thiazolidine-4-carboxylic acid or a salt thereof, and a 2-ethyl-2,4-dimethyl-(3)-thiazolidine-4-carboxylic acid or a salt thereof.

EXAMPLES

The present invention will be more specifically described by way of the following examples. However, these examples are not intended to limit the scope of the present invention.

Example I-1

A medium with the composition described below was prepared. 200 ml of the medium was placed in a 1-L Erlenmeyer flask. After the medium had been sterilized, it was inoculated with *Xanthobacter flavus* NCIB 10071. The obtained mixture was then subjected to a shaking culture at 30° C. for 48 hours. Thereafter, intact cells equivalent to 1.0 g of dried cells were obtained from the culture solution by centrifugation.

| Medium composition (pH 7.0) | |
|---|---|
| Glucose | 10 g |
| Polypeptone | 5 g |
| Yeast extract | 5 g |
| $KH_2PO_4$ | 1 g |
| $MgSO_4 \cdot 7H_2O$ | 0.4 g |
| $FeSO_4 \cdot 7H_2O$ | 0.01 g |

| -continued | |
|---|---|
| Medium composition (pH 7.0) | |
| $MnCl_2 \cdot 4H_2O$ | 0.01 g |
| Water | 1 L |

10.0 g (0.06 mol) of 2-methylcysteinamide hydrochloride as a racemic body was dissolved in 300 ml of water, and the obtained solution was then placed in a 500-ml flask. Thereafter, an aqueous manganese chloride solution was added thereto, such that the concentration of divalent Mn ions became 10 ppm. Thereafter, the intact cells corresponding to 1.0 g of dried cells were further added thereto. The mixture was stirred at 40° C. for 24 hours under nitrogen flow, so as to carry out hydrolysis. After completion of the reaction, the cells were removed from the reaction solution by centrifugation to obtain a supernatant. This supernatant was concentrated using a rotary evaporator, and the concentrate was then dissolved in 150 ml of methanol. Subsequently, 200 ml of acetone and 3.6 g (0.03 mol) of sodium carbonate were added thereto, and the mixture was stirred at room temperature for 16 hours, so as to carry out the reaction. Thereafter, the reaction solution was concentrated, and then supplemented with 50 ml of isobutyl alcohol and subjected to reflux conditions for 4 hours so as to extract soluble matters. After cooling, crystals that remained as insoluble matters were separated by filtration. The obtained crystals were recrystallized from ethanol to obtain colorless transparent crystals of 2,2,4-trimethylthiazolidine-4-carboxylic acid. The obtained 2,2,4-trimethylthiazolidine-4-carboxylic acid was dissolved in 100 ml of pure water, and the obtained solution was refluxed under nitrogen flow for 3 hours. Thereafter, the reaction solution was concentrated using a rotary evaporator, followed by drying under reduced pressure, to obtain 3.1 g (0.02 mol) of 2-methyl-L-cysteine. The yield of isolation was found to be 78 mol % relative to 2-methyl-L-cysteinamide contained in the racemic body that had been used for the reaction, and was found to be 39 mol % relative to 2-methylcysteinamide as a racemic body. Moreover, this solid was analyzed by liquid chromatography using an optical isomer separation column. As a result, the optical purity thereof was found to be 95% e.e. or more.

Example I-2

Example I-1 was repeated except that the biochemical asymmetric hydrolysis was carried out at 40° C. for 48 hours without the addition of the aqueous manganese chloride solution. As a result, 3.1 g (0.02 mol) of 2-methyl-L-cysteine was obtained similarly to Example I-1. The yield of isolation was found to be 78 mol % relative to the 2-methyl-L-cysteinamide, and was found to be 39 mol % relative to the 2-methylcysteinamide. The optical purity thereof was found to be 95% e.e. or more.

Example II-1

A medium with the composition described below was prepared. 200 ml of the medium was placed in a 1-L Erlenmeyer flask. After the medium had been sterilized, it was inoculated with *Xanthobacter flavus* NCIB 10071. The obtained mixture was then subjected to a shaking culture at 30° C. for 48 hours. Thereafter, intact cells equivalent to 1.0 g of dried cells were obtained from the culture solution by centrifugation.

| Medium composition (pH 7.0) | |
| --- | --- |
| Glucose | 10 g |
| Polypeptone | 5 g |
| Yeast extract | 5 g |
| $KH_2PO_4$ | 1 g |
| $MgSO_4 \cdot 7H_2O$ | 0.4 g |
| $FeSO_4 \cdot 7H_2O$ | 0.01 g |
| $MnCl_2 \cdot 4H_2O$ | 0.01 g |
| Water | 1 L |

10.0 g (0.06 mol) of 2-methylcysteinamide hydrochloride as a racemic body was dissolved in 300 ml of water, and the obtained solution was then placed in a 500-ml flask. Thereafter, an aqueous manganese chloride solution was added thereto, such that the concentration of divalent Mn ions became 10 ppm. Thereafter, intact cells corresponding to 1.0 g of dried cells were further added thereto. The mixture was stirred at 40° C. for 24 hours under nitrogen flow, so as to carry out hydrolysis. After completion of the reaction, the cells were removed from the reaction solution by centrifugation to obtain a supernatant. This supernatant was concentrated using a rotary evaporator, and the concentrate was then dissolved in 150 ml of methanol. Subsequently, 200 ml of acetone and 3.6 g (0.03 mol) of sodium carbonate were added thereto, and the mixture was stirred at room temperature for 16 hours, so as to carry out the reaction. Thereafter, the reaction solution was concentrated, and then supplemented with 50 ml of isobutyl alcohol and subjected to reflux conditions for 4 hours so as to extract soluble matters. After cooling, crystals that remained as insoluble matters were separated by filtration. The obtained filtrate was concentrated and dried using a rotary evaporator. The obtained concentrate was washed with 50 ml of hexane and then dried again to obtain 2,2,4-trimethylthiazolidine-4-carboxamide as a white solid. The obtained 2,2,4-trimethylthiazolidine-4-carboxamide was suspended in 100 ml of pure water, and was heated to reflux for 3 hours. Thereafter, the reaction solution was washed with 50 ml of diethyl ether twice. A water layer thereof was concentrated and dried, followed by drying under reduced pressure, to obtain 3.3 g (0.02 mol) of 2-methyl-D-cysteine. The yield of isolation was found to be 84 mol % relative to 2-methyl-D-cysteinamide contained in the racemic body that had been used for the reaction, and was found to be 42 mol % relative to 2-methylcysteinamide as a racemic body. Moreover, this solid was analyzed by liquid chromatography using an optical isomer separation column. As a result, the optical purity thereof was found to be 95% e.e. or more.

Example II-2

Example II-1 was repeated except that the biochemical asymmetric hydrolysis was carried out at 40° C. for 48 hours without the addition of the aqueous manganese chloride solution. As a result, 3.3 g (0.02 mol) of 2-methyl-D-cysteine was obtained similarly to Example II-1. The yield of isolation was found to be 84 mol % relative to the 2-methyl-D-cysteinamide, and was found to be 42 mol % relative to the 2-methylcysteinamide. The optical purity thereof was found to be 95% e.e. or more.

Example III-1

2.00 g of 2,2,4-trimethylthiazolidine-4-carboxamide hydrochloride prepared by the method described in Justus Liebigs Ann. Chem. (1966), 697, 140-157, was dissolved in 10 ml of 36% concentrated hydrochloric acid. The obtained solution was then heated to reflux at 105° C. for 1 hour, followed by concentration and drying. The thus obtained white solid was washed with isopropanol to obtain 1.62 g of 2-methylcysteine hydrochloride. This compound was converted into an aqueous solution, and the solution was passed through an anion exchange resin for desalinization. Thereafter, it was evaporated to dryness to obtain 1.27 g of 2-methylcysteine. The total amount of the obtained 2-methylcysteine was dissolved in 5 ml of methanol, and thereafter, 5 ml of acetone was added thereto, followed by heating to reflux at 56° C. Four hours later, the heating was terminated, and the reaction solution was concentrated and dried. The obtained white solid was then washed with acetone to obtain 1.32 g of 2,2,4-trimethylthiazolidine-4-carboxylic acid. The yield was found to be 80 mol % relative to the 2-methylcysteine hydrochloride as the raw material. The obtained 2,2,4-trimethylthiazolidine-4-carboxylic acid had the following physical properties:

2,2,4-trimethylthiazolidine-4-carboxylic acid

White Needle Crystals $^1$H-NMR (90 MHz, $D_2O$) δ [ppm] 3.70 (1H, d, J13.0 Hz), 3.30 (1H, d, J13.0 Hz), 1.83 (3H, s), 1.81 (3H, s), 1.71 (3H, s) elemental analysis $C_7H_{13}NO_2S$ (measured) C, 47.74; H, 7.51; N, 7.89; S, 18.28. (calculated) C, 47.98; H, 7.48; N, 7.99; O, 18.26; S, 18.30.

Example III-2

0.7 g of 2-methyl-L-cysteine hydrochloride was prepared by the method described in U.S. Pat. No. 6,403,830 specification. This compound was dissolved in 3 ml of methanol, and 0.3 g of anhydrous sodium carbonate was then suspended therein. Subsequently, 2 ml of acetone was added thereto, and the obtained solution was heated to reflux at 56° C. Two hours later, the heating was terminated, and the reaction solution was concentrated and dried. 1.1 g of the obtained white solid was then recrystallized from ethanol to obtain 0.58 g of 2,2,4-trimethylthiazolidine-4-L-carboxylic acid. The yield was found to be 81 mol % relative to the 2-methylcysteine hydrochloride as the raw material. The obtained 2,2,4-trimethylthiazolidine-4-carboxylic acid had the following physical properties:

2,2,4-trimethylthiazolidine-4-L-carboxylic acid

White Needle Crystals $^1$H-NMR (90 MHz, $D_2O$) δ [ppm] 3.70 (1H, d, J13.0 Hz), 3.30 (1H, d, J13.0 Hz), 1.83 (3H, s), 1.81 (3H, s), 1.71 (3H, s)

Example III-3

0.7 g of 2-methyl-L-cysteine hydrochloride was prepared by the method described in U.S. Pat. No. 6,403,830 specification. This compound was dispersed in 5 ml of cyclopentanone, and 0.45 g of triethylamine was further added thereto. A column that had been filled with 1 g of molecular sieve 4A was established, and the obtained solution was heated to reflux at 130° C. for 1 hour. Thereafter, the reaction solution was concentrated and dried, and the obtained yellow solid was then recrystallized from ethanol to obtain 0.53 g of 3-methyl-1-thia-4-aza-spiro[4,4]nonan-3-carboxylic acid. The yield was found to be 64.6 mol % relative to the 2-methylcysteine hydrochloride as the raw material. The obtained 3-methyl-1-thia-4-aza-spiro[4,4]nonan-3-carboxylic acid had the following physical properties: 3-methyl-1-thia-4-aza-spiro[4,4]nonan-3-carboxylic acid White Crystals $^1$H-NMR (90 MHz, CDCl$_3$) δ [ppm] 9.53 (1H, broad-s), 3.73 (1H, d, J12.8 Hz), 3.24 (1H, d, J12.8 Hz), 3.00~1.45 (14H, m) elemental analysis C$_9$H$_{15}$NO$_2$S (measured) C, 53.51; H, 7.65; N, 6.87; S, 15.88. (calculated) C, 53.70; H, 7.51; N, 6.96; O, 15.90; S, 15.93.

INDUSTRIAL APPLICABILITY

The process for producing an optically active 2-alkylcysteine or a salt thereof of the present invention is useful for inexpensively producing a high-quality optically active 2-alkylcysteine or a salt thereof that is important as an intermediate for production of various industrial chemicals, agricultural chemicals, pharmaceuticals, etc.

The 4-alkylthiazolidine-4-carboxylic acid or a salt thereof of the present invention is useful because this substance is an important intermediate for production of various industrial chemicals, agricultural chemicals, pharmaceuticals, etc. The production process thereof is useful for inexpensively producing this substance at high quality.

The process for producing an optically active 4-alkylthiazolidine-4-carboxamide or a salt thereof of the present invention is useful for inexpensively producing a high-quality optically active 4-alkylthiazolidine-4-carboxamide or a salt thereof that is an important substance acting as an intermediate for production of various industrial chemicals, agricultural chemicals, pharmaceuticals, etc.

The invention claimed is:

1. A process for producing an optically active 2-alkyl-L-cystein or a salt thereof from a 2-alkylcysteinamide or a salt thereof, which comprises allowing cells of microorganism or a treated product thereof having an activity of stereoselective hydrolysis of the amide bond of a 2-alkyl-L-cysteinamide or a salt thereof to act on a 2-alkylcysteinamide represented by the general formula (1) or a salt thereof, so as to generate a 2-alkyl-L-cysteine represented by the general formula (2) or a salt thereof;

allowing the generated 2-alkyl-L-cysteine or salt thereof and an unreacted 2-alkyl-D-cysteinamide represented by the general formula (3) or a salt thereof to react with an aldehyde or ketone represented by the general formula (4), or an acetal or ketal thereof, so as to derive therefrom a 4-alkylthiazolidine-4-carboxylic acid represented by the general formula (5) or a salt thereof and a 4-alkylthiazolidine-4-carboxamide represented by the general formula (6) or a salt thereof, respectively;

separating the 4-alkylthiazolidine-4-carboxylic acid represented by the general formula (5) or salt thereof from the mixture thereof; and hydrolyzing it for ring-opening to yield an optically active 2-alkyl-L-cysteine represented by the general formula (2) or a salt thereof, where in the general formulas (1), (2), (3), (5) and (6), R represents a C$_{1-4}$ lower alkyl; and in the general formulas (4), (5) and (6), each of R$_1$ and R$_2$ independently represents hydrogen or a C$_{1-4}$ lower alkyl, or R$_1$ and R$_2$ bind to each other to form a 5- to 8-membered alicyclic structure, provided that R$_1$ and R$_2$ do not simultaneously represent hydrogen.

2. A process for producing an optically active 2-alkyl-D-cystein or a salt thereof from a 2-alkylcysteinamide or a salt thereof, which comprises allowing cells of microorganism or a treated product thereof having an activity of stereoselective hydrolysis of the amide bond of a 2-alkyl-L-cysteinamide or a salt thereof to act on a 2-alkylcysteinamide represented by the general formula (1) or a salt thereof, so as to generate a 2-alkyl-L-cysteine represented by the general formula (2) or a salt thereof;

allowing the generated 2-alkyl-L-cysteine or salt thereof and an unreacted 2-alkyl-D-cysteinamide represented by the general formula (3) or a salt thereof to react with an aldehyde or ketone represented by the general formula (4), or an acetal or ketal thereof, so as to derive therefrom a 4-alkylthiazolidine-4-carboxylic acid represented by the general formula (5) or a salt thereof and a 4-alkylthiazolidine-4-carboxamide represented by the general formula (6) or a salt thereof, respectively;

separating the 4-alkylthiazolidine-4-carboxamide represented by the general formula (6) or salt thereof from the mixture thereof; and hydrolyzing it for ring-opening and amide hydrolysis to yield an optically active 2-alkyl-D-cysteine represented by the general formula (7) or a salt thereof, where in the general formulas (1), (2), (3), (5), (6) and (7), R represents a $C_{1-4}$ lower alkyl; and in the general formulas (4), (5) and (6), each of $R_1$ and $R_2$ independently represents hydrogen or a $C_{1-4}$ lower alkyl, or $R_1$ and $R_2$ bind to each other to form a 5- to 8-membered alicyclic structure, provided that $R_1$ and $R_2$ do not simultaneously represent hydrogen.

3. The process according to claim 1, wherein the microorganism having an activity of stereoselective hydrolysis of the amide bond of a 2-alkyl-L-cysteinamide or a salt thereof is a bacterium which belongs the genus *Xanthobacter*, the genus *Protaminobacter*, or the genus *Mycoplana*.

4. The process according to claim 1, wherein said R represents methyl.

5. The process according to claim 1, wherein said $R_1$ and $R_2$ both represent methyl.

6. The process according to claim 1, wherein a basic catalyst is used when the 2-alkyl-L-cysteine represented by the general formula (2) or salt thereof or the 2-alkyl-D-cysteinamide represented by the general formula (3) or salt thereof, is allowed to react with the aldehyde or ketone represented by the general formula (4), or an acetal or ketal thereof.

7. The process according to claim 1, wherein a dehydrating agent is used when the 2-alkyl-L-cysteine represented by the general formula (2) or salt thereof, or the 2-alkyl-D-cysteinamide represented by the general formula (3) or a salt thereof is allowed to react with the aldehyde or ketone represented by the general formula (4), or an acetal or ketal thereof.

8. The process according to claim 2, wherein the microorganism having an activity of stereoselective hydrolysis of the amide bond of a 2-alkyl-L-cysteinamide or a salt thereof is a bacterium which belongs the genus *Xanthobacter*, the genus *Protaminobacter*, or the genus *Mycoplana*.

9. The process according to claim 2, wherein said R represents methyl.

10. The process according to claim 2, wherein said $R_1$ and $R_2$ both represent methyl.

11. The process according to claim 2, wherein a basic catalyst is used when the 2-alkyl-L-cysteine represented by the general formula (2) or salt thereof, or the 2-alkyl-D-cysteinamide represented by the general formula (3) or salt thereof is allowed to react with the aldehyde or ketone represented by the general formula (4), or an acetal or ketal thereof.

12. The process according to claim 2, wherein a dehydrating agent is used when the 2-alkyl-L-cysteine represented by the general formula (2) or salt thereof, or the 2-alkyl-D-cysteinamide represented by the general formula (3) or a salt thereof, is allowed to react with the aldehyde or ketone represented by the general formula (4), or an acetal or ketal thereof.

* * * * *